United States Patent [19]
Kock et al.

[11] Patent Number: 5,849,803
[45] Date of Patent: Dec. 15, 1998

[54] METHOD OF TREATING ERECTILE DYSFUNCTION WITH NITROGLYCERINE

[76] Inventors: Nils G. Kock, Apotekaregatan 3, S-413 19, Göteborg; Gerhard Lycke, Annikas gata 4, S-421 67 Västra Frölunda, both of Sweden

[21] Appl. No.: 478,982

[22] Filed: Jun. 7, 1995

Related U.S. Application Data

[62] Division of Ser. No. 244,407, Sep. 14, 1988, abandoned.

[30] Foreign Application Priority Data

Sep. 2, 1988 [SE] Sweden ................................. 8803087

[51] Int. Cl.⁶ ......................... A61K 31/045; A61K 31/04
[52] U.S. Cl. ............................................. 514/727; 514/742
[58] Field of Search .............................................. 514/727

[56] References Cited

U.S. PATENT DOCUMENTS

| | | | |
|---|---|---|---|
| 4,472,376 | 9/1984 | Kamishita | 424/81 |
| 4,746,508 | 5/1988 | Carey et al. | 424/88 |
| 4,801,587 | 1/1989 | Voss et al. | 514/248 |

FOREIGN PATENT DOCUMENTS

| | | |
|---|---|---|
| 149254 | 7/1985 | European Pat. Off. . |
| 266968 | 5/1988 | European Pat. Off. . |
| 3637157 | 5/1987 | Germany . |
| 2095994 | 3/1981 | United Kingdom . |

OTHER PUBLICATIONS

Rudd., et al., *The Pharmacological Basis of Therapeutics*, Gilman et al. (Eds) 7th Ed., Chap. 32 pp. 784–785 (1985).
Turner, J.E., et al., "Prostaglandin $E_2$ in Tylose Gel for Cervical Ripening Before Induction of Labor" *J. Reprod. Med.* 32(11):815–821 (1987).
Andersson, K.E., et al., "Effects of Prostaglandin $E_2$ Applied Locally on Intravesical and Intraurethral Pressures in Women", *Eur. Urol.*, 4(5):366–369 (1978).
Axelsson, K., et al., "Blood Concentration of Lidocaine after Application of 2% Lignocaine Gel in the Urethra", *Br. J. Urol.*, 55(1):64–68 (1983).
Owen, J., et al., Transcutaneous Nitroglycerine Enhances the Quality of Erections in Impotent Men. Results of a Controlled Trial, *J. Urol.*, 137, 201A, abstract 392 (1987).
Mahler, J.C., et al., "Intraurethral Cocaine Administration", *JAMA* 259(21):3126 (1988).
Milco, St. M., "Administration intra–uretrale de l'hormone masculine, chez l'homme", *Bulletin Et Memories De La Societe Roumaine D'Endocrinologie* 5:436–437 (1939). (Translation provided).

Chemical Abstracts, vol. 111, (1989) Abs. 1404820.
Malloy et al., "Pharmacological Treatment of Impotence," *Urologic Clinics of North America*, 14(2) (May 1987).
Klinge et al, "Comparative Study of Some Isolated Mammalian Smooth Muscle Effectors of Penile Erection," *Acta Physiol. Scand.* 100:354–367 (Feb. 1987).
Hedlund et al., "Contraction and Relaxation Induced by Some Prostanoids in Isolated Human Penile Erectile Tissue and Cavernous Artery," *The Journal of Urology*, 134:1245–1250 (Dec. 1985).
Barbanti et al., "Relaxation of Isolated Corpus Cavernosum Induced by Smooth Muscle Relaxant Drugs," *Urological Research*, 16(4):299–302 (1988).
Yamamura et al., "High–Performance Liquid Chromatographic Assay for Prostaglandin $E_1$ in Various Ointment Vehicles," *J. Chromatography*, 303:165–172 (1984).
Sundaram, M.B.M., "Seizures After Intraurethral Instillation of Lidocaine," *Canad. Med. Assn. J.*, 137:219–220 (1987).
Robinette et al., "Intracorporal Injection of Papaverine and Phentolamin in the Management of Impotence," *Br. J. Urology*, 58:692–695 (1986).
Zorgniotti et al., "Auto–Injection of the Corpus Cavernosum with A Vasoactive Drug Combination for Vasculogenic Impotence," *J. Urol.*, 133:39–41 (1985).
"Intracavernous Injections for Impotence," *The Medical Letter*, 29(751):95–96 (Oct. 1987).
Brindley, G.S., "Cavernosal Alpha–Blockade: A New Technique for Investigating and Treating Erectile Impotence," *Brit. J. Psychiat.*, 143:332–337 (1983).
Brindley, G.S., "Pilot Experiments on the Actions of Drugs Injected Into the Human Corpus Cavernosum Penis," *Br. J. Pharmac.*, 87:495–500 (1986).
Ishii, N., et al., "Studies On Male Sexual Impotence Report 18: Therapeutic Trial with Prostaglandin E1 for Organic Impotence," *Japanese J. Urol.*, 77(6):954–955 (1986).
Stackl, et al., "Intracavernous Injection of Prostaglandin E1 in Impotent Men," *J. Urol.*, 140:66–68 (1988).
Virag, R., "Intracavernous Injection of Papaverine for Erectile Failure," *The Lancet*, 2:938 (1982).
Waldhauser et al., "Efficiency and Side Effects of Prostaglandin E1 in the Treatment of Erectile Dysfunction," *J. Urol.*, 140:525–527 (1988).
Derwent Abstract to San Starr KK, Jun. 12, 1984.

*Primary Examiner*—Theodore J. Criares
*Attorney, Agent, or Firm*—Dianne E. Reed; Bozicevic & Reed LLP

[57] ABSTRACT

Lipophilic active substance composition and its use in a new method of treating erectile dysfunction by administration of nitroglycerine together with a hydrophilic vehicle and optionally an antibacterial agent into the urethra.

12 Claims, 1 Drawing Sheet

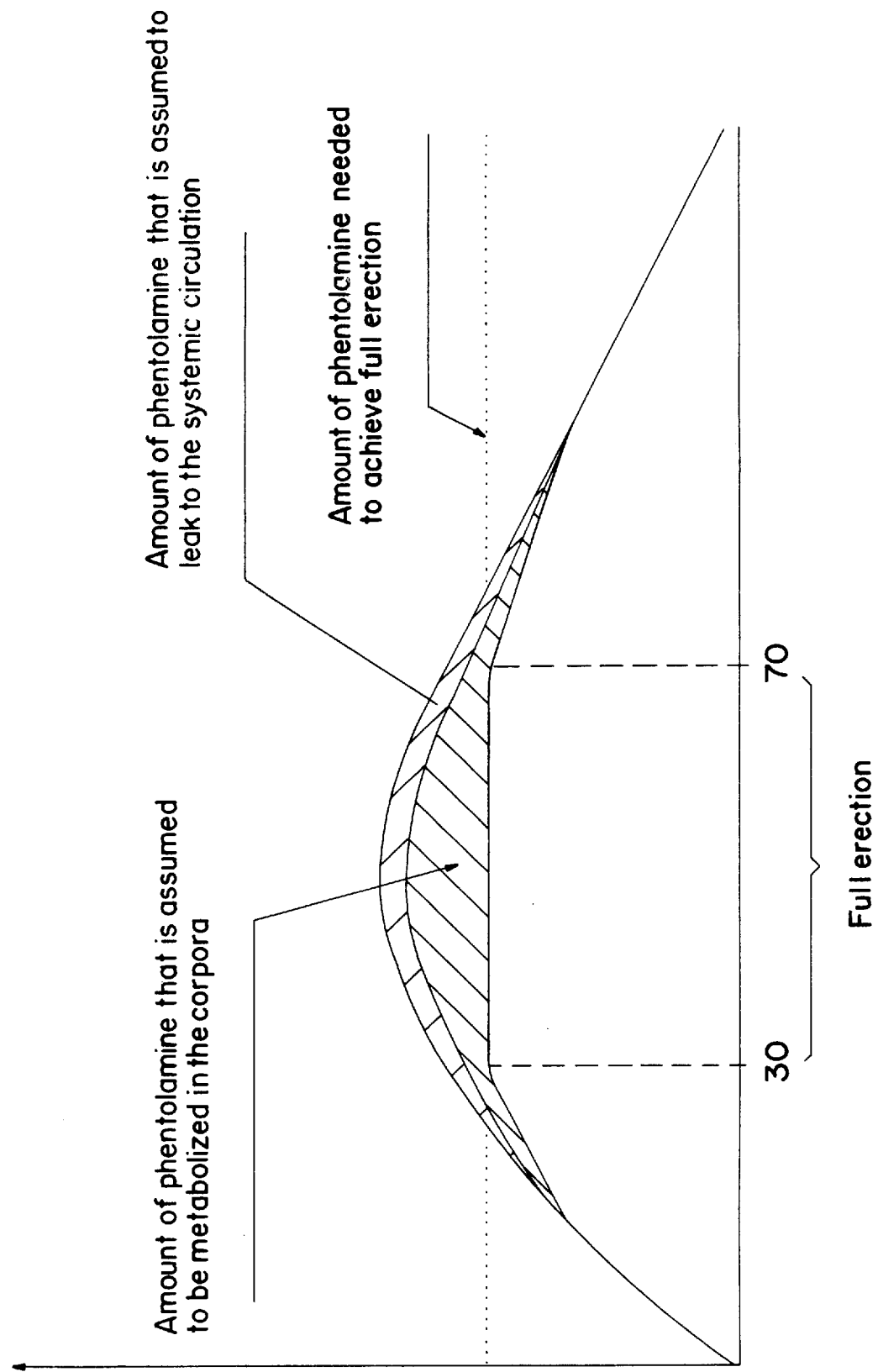

METHOD OF TREATING ERECTILE DYSFUNCTION WITH NITROGLYCERINE

This application is a division application of U.S. patent application Ser. No. 07/244,407, filed Sep. 14, 1988 now abandoned.

FIELD OF THE INVENTION

This invention relates to a lipophilic active substance composition and its use in a new method of treating erectile dysfunction by administration thereof, optionally together with a hydrophilic vehicle and optionally an antibacterial agent into the urethra.

BACKGROUND OF THE INVENTION

Normal erection activity involves the coordination of a complex series of physiological and psychological factors. Anything that affects any one of these systems can cause impotence. Psychogenic impotence can be caused by e.g. anxiety, depression, tension and stress.

Physical impotence occurs when diseases or injury affects the nerves, blood vessels or hormones that control erectile ability. The major causes of physical impotence in the United States are diabetes mellitus, vascular diseases, impotence following radical surgery, spinal cord injury and other traumas, other endocrine problems and multiple sclerosis. Other causes include prostate infections, drug abuse, alcoholism and side effects of prescription medicines. Even smoking can interfere with normal erections.

It is estimated that about 10 million men in the United States suffer from impotence. Above the age of 60 about one of three are no longer able to achieve a suitable erection.

There are several medical treatment alternatives currently available depending on the nature and cause of the impotence problem, such as therapy with Yohimbine, an Indian tree bark extract, thought to chemically stimulate the nerves in penis that control erections. Early reports indicate that normal erection is restored in 20–25 percent of the patients, but the effect is disputable. Side effects may include dizziness, nausea, nervousness and headaches.

For some men with low male hormone (testosterone) levels treatment with testosterone injections or pills may be beneficial. However, most patients do not have low testosterone levels and will not benefit from supplemental hormones. The side effects of testosterone treatment are several.

In recent years patients with erectile dysfunction of various origin have been treated by intracorporeal injection of various drugs. One such medicament is papaverin, which in small amounts dilates the arterial blood vessels and decreases the venous drainage (Virag R., Intracavernous injection of papaverin for erectile failure. Letter to the editor. Lancet 1982; 2:938). Brindley, G. S. describes in Brit. J. Psychiat. (1983), 143, 332–337 a new technique for investigating and treating erectile impotence by intracavernous self-injection of small doses of phenoxybenzamine or phentolamine. The doses as used for intracorporeal injection are about 2–10 mg of phenoxybenzamine and about 0.5–1.5 mg of phentolamine.

The side effects of self-injection of medication are the risk of infection, bruises, fibrosis and scarring with permanent changes inside the penis. There is also a risk of painful longstanding erection (Priapism).

It is further known that intravenous or intramuscular injection of phentolamine in moderate doses can cause an excessive fall in blood-pressure due to peripheral vasodilatation which puts the patient into a state of circulatory shock.

Experimentally it has been shown in some cases that cutaneous application of nitroglycerine paste to some extent can enhance the quality of erection.

Further, surgical implantation of penile prosthesis have been performed when simpler treatments are unsuccessful. However, all surgical penile prosthetic implants carry a high risk of infection. Other complications of surgery include temporary urinary retention, pain, bleeding, scarring, mechanical failure and extrusion of the implant.

SUMMARY OF THE INVENTION

Therefore, the objects of the invention was to provide a method and a composition for the treatment of erectile dysfunction, which should be non-invasive, easy to use, have no significant side effects (short or longterm), be reasonably cheap, give a penile rigidity sufficient for vaginal penetration during a suitable time (20–30 minutes), be self-limiting, i.e. it should not be possible to overuse the drug(s) by taking more than one dose at a time (to avoid the risk of priapism).

These objects are achieved by a lipophilic active substance composition and its use in a method of treating erectile dysfunction by administration thereof, optionally together with a hydrophilic vehicle and optionally an antibacterial agent into the urethra.

DESCRIPTION OF THE PREFERRED EMBODIMENTS

Hitherto it has been commonly believed that the urethral mucosal membrane does not allow transport of molecules across the same as waste products are transported via the urinary tract. Surprisingly and against all theories we have discovered that it is possible to administer pharmacologically active substances via the urethral mucosa into the corpora cavernosa of the human penis.

Previously, drugs of different nature than those of the present invention have been administered to the urethra for purposes of local disinfection and prophylaxis against venereal diseases and to induce local anesthesia. Administration of drugs into the urethra to reach the corpora cavernosa and to achieve effect has not been performed previously since the fact that this could be achieved was not known until the present invention.

Psychological erectile dysfunction is, at least partially, caused by an increased sympathetic tone that prevents the activation of the erection mechanism in the corpora cavernosa. Therefore, as mentioned above, one approach has been to inject an α-receptor blocker, such as phentolamine and phenoxybenzamine, intracorporeally. However, injection of phentolamine only gives a short lasting erection while phenoxybensamine has a long duration but is believed to have severe side effect and presents a number of risks.

By experimental results we have found that when phentolamine is administered in an amount of 10–200 mg, preferably 50–60 mg per urethra in a volume of 1–6 ml, in general 2–3 ml, a full and satisfactory erection occurs without any obvious systemic side effects. (The dose used for intracorporeal injection of phentolamine is 0.5–1,5 mg.) The same desired results can also be achieved using phenoxybenzamine in high doses, 50–300 mg, preferably 100–150 mg per urethra, compared to the dose used for intracorporeal injection which is above about 2–10 mg. Another well suited α-receptor blocker candidate for this purpose is prazosine in an amount of about 20–200 mg, preferably 30–70 mg. Other α-receptor blockers might also be suitable.

According to our invention a large dose of the active substance is administered, preferably instilled, into the urethra and the slow uptake via the urethral mucosa to the corpora cavernosa gives a longer effect than the intracorporeal injections according to prior art.

Moreover, the active substance administered according to the present invention can also comprise other $\alpha_1$ and $\alpha_2$-blocking agents and vasoactive intestinal polypeptide, prostaglandins, preferably $PGE_1$, $PGE_2$ and $PGF_2$, and nitroglycerine. The active substances must fulfil all the above listed objects of the present invention and also, which is very important, be fat soluble in order to pass through the mucosal membrane of the urethra.

When nitroglycerine is used as the active substance it should be administered in a dose not exceeding 5 mg per urethra because of the risk of blood-pressure fall. The dose range according to the invention is 0.5–5 mg, preferably 0.5–2,5 mg. This dose, however, is very high compared to the dose of nitroglycerine normally given to Angina pectoris patients which is 0.25 mg to 0.5 mg.

The present invention also provides compositions containing two or more of the active substances, i.e. two or more of the α-receptor blockers, vasoactive intestinal polypeptide, prostaglandins and nitroglycerine, due to their different affinity for the α-receptor blockers $\alpha_1$ and $\alpha_2$. Such compositions are e.g. phentolamine and nitroglycerine, phenoxybenzamine and nitroglycerine, prazosine and nitroglycerine, all in the dose stated above. Furthermore, for possible synergistic effects phentolamine+phenoxybenzamine and phentolamine+prazosine and phenoxybenzamine and prazosine, respectively, can be administered together with nitroglycerine.

The purpose of the combination between α-receptor(s) and nitroglycerine is that nitroglycerine gives a synergistic effect with α-receptor blockers in that it obstructs sympathicus due to a local sympaticolytical effect and causes vasodilatation via a mecanism different from that of α-receptor blockers. Nitroglycerine entails more rapid absorbation and therefore gives an earlier effect.

Moreover, the invention also comprises a composition which in addition to the fat soluble active substance(s) comprises a hydrophilic vehicle and optionally an antibacterial agent. The purpose of the hydrophilic vehicle, such as macrogols and/or fat-free cream or ointment bases, is not only to control the uptake via the urethral membrane into the corpora cavernosa and keep the active substance(s) in the urethra but also presumably to enhance the uptake or passage of the urethral mucosa by forcing the fat soluble substances into the corpora cavernosa due to the fact that the vehicle is hydrophilic and the fat soluble active substance(s) tend(s) to migrate to and through the membrane lipids rather than to stay in the hydrophilic environment. Thus, the purpose of the combination of the lipophilic active substance(s) and the hydrophilic vehicle is keeping the receptors activated (blocked) in a controlled way and under a longer period of time.

The invention will now be described by way of an example with reference to the accompanying drawing.

EXAMPLE

FIG. 1 is a graph showing the principles of the relationship between amount of phentolamine on the vertical axis and the duration of time on the horisontal axis. The patient was initially given 60 mg of the α-receptor blocker phentolamine administered into the urethra and thereafter the penile rigidity was checked. During the peak of the curve, between 30 and 70 minutes from the administration of the active substance, full erection was achieved. The level of phentolamine needed to achieve full erection is shown by the dotted line in FIG. 1. The peak area above the dotted line is divided into two sections showing the amount of phentolamine assumed to be metabolized in the corpora cavernosa and the amount of phentolamine assumed to leak to the systemic circulation, respectively. Thus, the erection achieved by administration of phentolamine according to the present invention is considerably longer than the time period achieved with injections according to prior art.

It is assumed that the transport capacity of the urethral mucosa only slightly exceeds the capability of the corpora cavernosa to metabolize phentolamine. The abundant phentolamine, i.e. above the dotted line in FIG. 1 is mainly metabolized locally in the corpora cavernosa and only a minor part is assumed to leak to the systemic circulation. If a lower dose of phentolamine is used the rate of transportation over the urethral mucosa will be less than the rate of metabolization in the corpora cavernosa and therefore a sufficient number of α-receptors will not be activated to achieve a full erection. A dose as high as 200 mg is possible, but the preferred range is between 50–60 mg, considering the risk of circulatory shock.

Thus, the present invention provides a new method, a composition and use thereof for the treatment of erectile dysfunction avoiding the prior art drawbacks and giving an opportunity for millions of impotent men to have a sex life that is as close to normal as possible.

Table 1 shows the results of tests to treat impotence in cystectomized patients by the application of different substances per urethra.

TABLE I

RESULTS OF TESTS TO TREAT IMPOTENCE IN CYSTECTOMIZED PATIENTS
BY THE APPLICATION OF DIFFERENT SUBSTANCES PER URET

| Substances | No of patients | Doses | Results |
|---|---|---|---|
| Verapamil | 1 | 10 mg | 0 |
| Verapcimil | 1 | 15 mg | 0 |
| Salbutamol | 1 | 1,6 mg | + |
| Terbutalin | 1 | 1,0 mg | + |
| Papaverine | 2 | 100 mg | 0 |
| Papaverine | 1 | 210 mg | + |
| Phentolamine | 2 | 10 mg | + |
| Phentolamine | 1 | 10 mg | ++ |

TABLE I-continued

RESULTS OF TESTS TO TREAT IMPOTENCE IN CYSTECTOMIZED PATIENTS
BY THE APPLICATION OF DIFFERENT SUBSTANCES PER URET

| Substances | No of patients | Doses | Results |
|---|---|---|---|
| Phentolamine | 1 | 60 mg | +++ (not cystectomized) |
| Phenoxybenzamine | 1 | 50 mg | + |
| Phenoxvbenzamine | 1 | 50 mg | ++ |
| Nitroqlycerin | 5 mg | + | |
| Phentolamine + nitroglycerin | 2 | 10 mg + 2,5 mg | ++ |
| Phentolamine +nitroglycerin | 4 | 20 mg + 2,5 mg | ++ |
| Phentolamine + nitroglycerin | I | 20 mg + 5 mg | ++ |
| Phentolamine + nitroglycerin | 1 | 20 mg + 5 mg | ++(+) |
| Phentolamine + nitroglycerin | 3 | 30 mg + 2,5 mg | ++ |
| Phentolamine + nitroglycerin | 1 | 30 mg + 2,5 mg | ++(+) |
| Phentolamine + nitroglycerln | 1 | 30 mg + 5 mg | ++ |
| Phentolamine + nitroglycerin | 1 | 30 mg + 5 mg | ++(+) |
| Phentolamine + nitroglycerin | 3 | 40 mq + 2,5 mg | ++ |
| Phenoxybenzamine + nitroglycerin | 1 | 50 mg + 1,5 mg | + |
| Phenoxybenzamine + nitroglycerin | 1 | 50 mg + 1,5 mg | ++ |
| Phenoxybenzamine + nitroglycerin | 1 | 100 mg + 1,5 mg | ++ |
| Phenoxybenzamine + nitroglycerin | 1 | 100 mg + 1,5 mg | ++(+) |
| Phentolamine + Phenoxybenzamine + nitroglycerin | 1 | 10 mg + 50 mg + 1,5 mg | ++ |
| Phentolamine + Phenoxybenzamine + nitroglycerin | 1 | 10 mg + 100 mg + 1,5 mg | ++ |
| Phentolamine + Phenoxybenzamine + nitroglycerin | 1 | 20 mg + 50 mg + 2,5 mg | + |
| Phentolamine + Phenoxybenzamine + nitroglycerin | 1 | 30 mg + 50 mg + 1,5 mg | ++ |

Summary of scores:
5 = 0
8 = +
21 = ++
5 = +++
In 33 patients the treatment was given in fluid-form, while in 6 patients the substances were dissolved in ointment.
Three patients who were given a dose for use at home reported that they succeeded in completing intercourse.
Side-effects were seen in 12 patients. Four patients experienced a short-lasting drop in blood pressure, all of them had had a high nitroglycerin dose. Eight patients developed local irritation. In 7 of these the irritation was caused by the alcohol in which the nitroglycerin was dissolved. In one patient with local irritation concentrated phentolamine was used (30 mg/ml).
All 5 patients with the effect-score ++(+) and most of those with score ++ had a penile rigidity that to our judgement was sufficient for vaginal penetration. Thus these tests indicate that per urethram treatment of ED can be useful.

We claim:

1. A method of treating erectile dysfunction wherein a composition comprising a therapeutically effective amount of nitroglycerine and a hydrophilic vehicle is administered into the urethra.

2. A method according to claim 1, wherein said composition additionally comprises vasoactive intestinal polypeptide.

3. A method according to claim 1, wherein nitroglycerine is administered in an amount of at most 5 mg.

4. A method according to claim 1 wherein nitroglycerine is administered in an amount of 0.5–1.5 mg.

5. A method according to claim 1, wherein said composition is administered into the urethra in a volume of 1–6 ml.

6. A method according to claim 1, wherein said composition additionally comprises a prostaglandin.

7. A method according to claim 1, wherein said composition additionally comprises an α-receptor blocker.

8. A method according to claim 7, wherein said α-receptor blocker is selected from the group consisting of phentolamine, phenoxybenzamine and prazosine.

9. A method according to claim 1, wherein the active substance is administered by instillation.

10. A method according to claim 1 wherein said method additionally comprises administering an antibacterial agent into the urethra.

11. A method according to claim 6 wherein said prostaglandin is prostaglandin $E_1$.

12. A method according to claim 6 wherein said prostaglandin is prostaglandin $E_2$.

* * * * *